United States Patent
Hall et al.

(12)
(10) Patent No.: US 6,276,795 B1
(45) Date of Patent: Aug. 21, 2001

(54) PROTECTIVE EYEWEAR WITH ADJUSTABLE STRAP

(75) Inventors: James Hall, Lincoln, RI (US); John E. Salce, Auburn; Raoul Desy, Sturbridge, both of MA (US)

(73) Assignee: Aearo Company, Southbridge, MA (US)

( * ) Notice: Subject to any disclaimer, the term of this patent is extended or adjusted under 35 U.S.C. 154(b) by 0 days.

(21) Appl. No.: 09/542,238

(22) Filed: Apr. 4, 2000

Related U.S. Application Data

(63) Continuation-in-part of application No. 09/032,505, filed on Feb. 26, 1998, now Pat. No. 6,149,268, which is a continuation-in-part of application No. 08/806,595, filed on Feb. 26, 1997, now Pat. No. 6,024,446, and a continuation-in-part of application No. 08/806,832, filed on Feb. 26, 1997, now Pat. No. 5,825,455, and a continuation-in-part of application No. 08/770,920, filed on Dec. 20, 1996, now Pat. No. 5,909,267, and a continuation-in-part of application No. 08/641,901, filed on May 2, 1996, now abandoned.

(51) Int. Cl.⁷ .............................. G02C 11/08; A61F 9/02
(52) U.S. Cl. ................... 351/62; 351/41; 2/431; 2/437
(58) Field of Search ..................... 351/41, 43, 44, 351/62, 158; 2/426–429, 435–437, 448, 449, 440, 431

(56) References Cited

U.S. PATENT DOCUMENTS

| | | | |
|---|---|---|---|
| D. 135,237 | 3/1943 | Bausch | D57/1 |
| D. 140,506 | 3/1945 | Joyce | D16/110 |
| D. 141,029 | 4/1945 | Splaine | D57/1 |
| D. 141,193 | 5/1945 | Baratelli | D57/1 |
| D. 144,560 | 4/1946 | Hansen | D57/1 |
| D. 163,869 | 7/1951 | Hinman | D57/1 |
| D. 198,052 | 4/1964 | Petitto | D57/1 |
| D. 198,996 | 8/1964 | Lissac | D57/1 |
| D. 199,150 | 9/1964 | Carmichael | D57/1 |
| D. 199,932 | 12/1964 | Shindler | D57/1 |
| D. 199,933 | 12/1964 | Shindler | D57/1 |
| D. 201,393 | 6/1965 | Thomas | D57/1 |
| D. 202,129 | 8/1965 | Marchi | D57/1 |
| D. 203,136 | 12/1965 | Shindler | D57/1 |
| D. 204,957 | 5/1966 | Dym | D57/1 |
| D. 228,028 | 7/1973 | Leblanc et al. | D57/1 |
| D. 228,583 | 10/1973 | Leblanc | D57/1 |
| D. 231,260 | 4/1974 | Jelinek | D57/1 |

(List continued on next page.)

FOREIGN PATENT DOCUMENTS

| | | |
|---|---|---|
| 485155 | 7/1952 | (CA) . |
| 1185637 | 8/1959 | (FR) . |
| 1247974 | 2/1961 | (FR) . |

*Primary Examiner*—Huy Mai
(74) *Attorney, Agent, or Firm*—Cantor Colburn LLP

(57) ABSTRACT

Safety eyewear is presented which is provided with particulate and liquid sealing around a frame containing lens/lenses and having temples that provide adjustment of the eyewear to a pantoscopic angle. The eyewear is provided with an adjustable strap assembly for better fit to the wearer's head. The eyewear lens/frame includes a plurality of projections that define various pantoscopic angles. The temple end piece includes a set of recesses that engage the projections formed on the lens/frame which temple end piece is rotated relative to the lens/frame to set the pantoscopic angle. The adjustable strap assembly further adjust the fit of the eyewear and can be unbuckled for snaplocked attachment of the eyewear directly to other safety equipment such as noise suppression ear muffs, communication head phones, breathing masks and the like. A plurality of ventilation channels is disposed on the frame to provide indirect ventilation. The frame includes a skirt which is designed to prevent unwanted foreign matter, including liquids, from entering underneath the eyewear and making contact with the eyes of a user.

24 Claims, 11 Drawing Sheets

U.S. PATENT DOCUMENTS

| | | | |
|---|---|---|---|
| D. 270,165 | 8/1983 | Burns | D16/119 |
| 289,740 | 12/1883 | Willson et al. | 351/140 |
| D. 323,333 | 1/1992 | Jannard et al. | D16/112 |
| D. 354,067 | 1/1995 | Luzlbauer | D16/112 |
| D. 358,828 | 5/1995 | Jannard et al. | D16/101 |
| 836,599 | 11/1906 | McKee et al. | 351/140 |
| 1,032,488 | 7/1912 | Marcher | 351/121 |
| 1,119,811 | 12/1914 | Day | 351/121 |
| 1,181,365 | 5/1916 | Beaudry | 351/121 |
| 1,189,986 | 7/1916 | Merry | 351/121 |
| 1,217,035 | 2/1917 | McDowell | 351/112 |
| 1,250,703 | 12/1917 | Hamilton et al. | 351/112 |
| 1,274,870 | 8/1918 | Golding | 351/112 |
| 1,278,190 | 9/1918 | Martin | 351/112 |
| 1,294,390 | 2/1919 | Burke | 351/116 |
| 2,004,005 | 6/1935 | McDanal | 351/140 |
| 2,537,047 | 1/1951 | Gatten | 351/159 |
| 2,630,569 | 3/1953 | Baratelli et al. | 351/121 |
| 3,218,765 | 11/1965 | Volk | 451/42 |
| 3,233,249 | 2/1966 | Baratelli et al. | 2/443 |
| 3,233,250 | 2/1966 | Jonassen | 351/121 |
| 3,283,446 | 11/1966 | Feinbloom | 451/42 |
| 3,394,980 | 7/1968 | Dym | 351/41 |
| 3,526,449 | 9/1970 | Bolle et al. | 351/41 |
| 3,544,204 | 12/1970 | Bienenfeld | 351/118 |
| 3,605,116 | 9/1971 | Simpson et al. | 351/169 |
| 3,623,800 | 11/1971 | Volk | 351/159 |
| 3,691,565 | 9/1972 | Galonek | 2/144 |
| 3,708,224 | 1/1973 | Lindblom | 351/62 |
| 3,722,986 | 3/1973 | Tagnon | 351/156 |
| 3,907,410 | 9/1975 | Richmond et al. | 351/119 |
| 3,950,082 | 4/1976 | Volk | 351/169 |
| 4,002,439 | 1/1977 | Volk | 451/42 |
| 4,240,178 | 12/1980 | Wichers | 351/62 |
| 4,564,272 | 1/1986 | Rinnooy Kan | 351/47 |
| 4,630,906 | 12/1986 | Bammert et al. | 351/159 |
| 4,670,915 | 6/1987 | Evans | 2/450 |
| 4,674,851 | 6/1987 | Jannard | 2/428 |
| 4,683,587 | 7/1987 | Silverman | 381/25 |
| 4,741,611 | 5/1988 | Burns | 351/44 |
| 4,786,125 | 11/1988 | Magarinos et al. | 351/47 |
| 4,810,080 | 3/1989 | Grendol et al. | 351/41 |
| 4,824,233 | 4/1989 | Jannard | 351/47 |
| 4,843,655 | 7/1989 | Hegendorfer | 2/449 |
| 4,859,048 | 8/1989 | Jannard | 351/159 |
| 4,867,550 | 9/1989 | Jannard | 351/47 |
| 4,955,087 | 9/1990 | Perez et al. | 351/41 |
| 4,955,706 | 9/1990 | Schmidthaler et al. | 351/41 |
| 4,977,627 | 12/1990 | Metcalfe et al. | 2/437 |
| 4,978,182 | 12/1990 | Tedesco | 359/15 |
| 5,032,017 | 7/1991 | Bolle et al. | 351/116 |
| 5,050,981 | 9/1991 | Roffman | 351/177 |
| 5,208,614 | 5/1993 | Jannard | 351/41 |
| 5,235,357 | 8/1993 | Winthrop et al. | 351/159 |
| 5,278,999 | 1/1994 | Brown et al. | 2/209 |
| 5,357,292 | 10/1994 | Wiedner | 351/105 |
| 5,379,463 | 1/1995 | Schleger et al. | 2/431 |
| 5,381,192 | 1/1995 | Canavan et al. | 351/118 |
| 5,387,949 | 2/1995 | Tackles | 351/121 |
| 5,418,581 | 5/1995 | Conway | 351/116 |
| 5,426,473 | 6/1995 | Riehm | 351/121 |
| 5,457,505 | 10/1995 | Canavan et al. | 351/120 |
| 5,511,251 | 4/1996 | Brakas | 2/452 |
| 5,519,896 | 5/1996 | Ford | 2/436 |
| 5,526,070 | 6/1996 | Simioni | 351/121 |
| 5,617,588 | 4/1997 | Canavan et al. | 2/428 |
| 5,659,381 | 8/1997 | Simioni | 351/120 |
| 5,666,663 | 9/1997 | Bolle | 2/10 |
| 5,724,119 | 3/1998 | Leight | 351/158 |
| 6,105,177 * | 8/2000 | Paulson et al. | 2/431 |

* cited by examiner

PROTECTIVE EYEWEAR WITH ADJUSTABLE STRAP

CROSS-REFERENCE TO RELATED APPLICATION

This is a continuation-in-part of application Ser. No. 09/032,505, filed Feb. 26, 1998, now U.S. Pat. No. 6,149,268, which is a continuation-in-part of application Ser. No. 08/641,901 filed May 2, 1996, now abandoned, application Ser. No. 08/770,920, filed Dec. 20, 1996, now U.S. Pat. No. 5,909,267, application Ser. No. 08/806,595, filed Feb. 26, 1997, now U.S. Pat. No. 6,024,446, and Ser. No. 08/806,832, filed Feb. 26, 1997 now U.S. Pat. No. 5,825,455.

FIELD OF THE INVENTION

This invention relates generally to eyewear. More particularly, this invention relates both to plano (that is non corrective or zero power) and prescription eyewear for use in safety and recreational applications (i.e., sports and/or hostile environments) with adjustable strap temples which optionally permit the secure attachment of other safety equipment such as ear muffs or head phones.

BACKGROUND OF THE INVENTION

Protective eyewear, both prescription and piano (that is non corrective or zero power) is available in the market place for both safety and recreational (i.e., sports) applications. Such eyewear is exemplified in U.S. patent application Ser. No. 08/641,901 filed May 2, 1996, which is assigned to the assignee hereof, all of the contents of which are incorporated herein by reference. This eyewear comprises a pair of spectacles which includes a lens attached to a pair of temples. The lens has a surface which is created by rotating an aspheric shape about an axis which is offset from an axis of the aspheric shape. Preferably, the aspheric shape is an ellipse and more preferably the resultant lens will have a cross-section in the horizontal meridian which is a segment of an ellipse and a cross-section in the vertical meridian which is a segment of a circle. This lens exhibits a high degree of wrap and so provides extensive protection without the need for side shields.

Of course, many other prior art protective eyewear is known, all of the eyewear generally utilizing a pair of rigid or semi-rigid temples which extend outwardly from the lenses or a lens frame. Examples of other protective spectacles of this type include U.S. Pat. Nos. 4,867,550; 4,741,611; 4,674,851; 4,859,048; 5,381,192 and 5,032,017, all of the contents of these patents being incorporated herein by reference.

One perceived problem not addressed by the prior art is that the prior art protective spectacles do not sufficiently protect the eyes from particulates that exist in dusty, dirty work environments. In addition, certain liquids present in various environments pose a risk in that liquids may splash in the face of the user and more specifically in the eyes of the user. Both of these problems are also present for some sport environments. Currently, it is known that most common eye injuries in the industrial workplace are a result of these aforementioned particulates or liquids entering the area immediately adjacent to the eye. Therefore, there is a perceived need to develop eyewear that will keep particulate matter and liquids away from the eye. Additionally, in hostile environments, there is often a need to wear safety eyewear in conjunction with other safety equipment such as noise suppression ear muffs or communication head phones without disrupting the particulate and liquid seal of the eyewear or the seal of the other safety device or devices. Therefore, there is an additionally perceived need for a method of attachment of the eyewear to other safety gear without affecting the seals of the individual safety items as is presently unavoidable with prior art temples associated with prior art safety and protective spectacles.

SUMMARY OF THE INVENTION

The above discussed and other drawbacks and deficiencies are overcome or alleviated by the eyewear of the present invention. An eyewear having a frame, a lens detachably attached to the frame and a strap assembly is disclosed. The frame and lens form at least one opening to allow ventilation. A resilient flange is provided along the periphery of the frame. In one embodiment, a plurality of L-shaped channels are provided to provide indirect ventilation. An end piece having a cylindrical extension detachably attaches the strap lens and frame. A head disposed on the cylindrical extension rotates to contact the frame and urge the outer periphery of the lens against a protrusion on the frame to retain the lens on the frame.

The frame has a skirt which is preferably integrally formed therewith and extends around a periphery of the frame. The skirt includes a beveled surface which extends outwardly away from the first side of the frame and a flange element extending around the beveled surface about the periphery of the frame. The skirt is preferably integrally formed with the remaining portions of the frame and is intended to prevent unwanted foreign matter from entering underneath the device and contacting the eyes of a user. The skirt is contoured to seat substantially flush against the face of the user so that particulate, liquids and other undesirable matter are prevented from freely entering underneath the frame and contacting the eyes of the user.

The above-discussed and other features and advantages of the present invention will be appreciated and understood by those skilled in the art from the following detailed description and drawings.

BRIEF DESCRIPTION OF THE DRAWINGS

Referring to the FIGURES wherein like elements are numbered alike in the several FIGS.

DESCRIPTION OF THE PREFERRED EMBODIMENT

Figure 1:
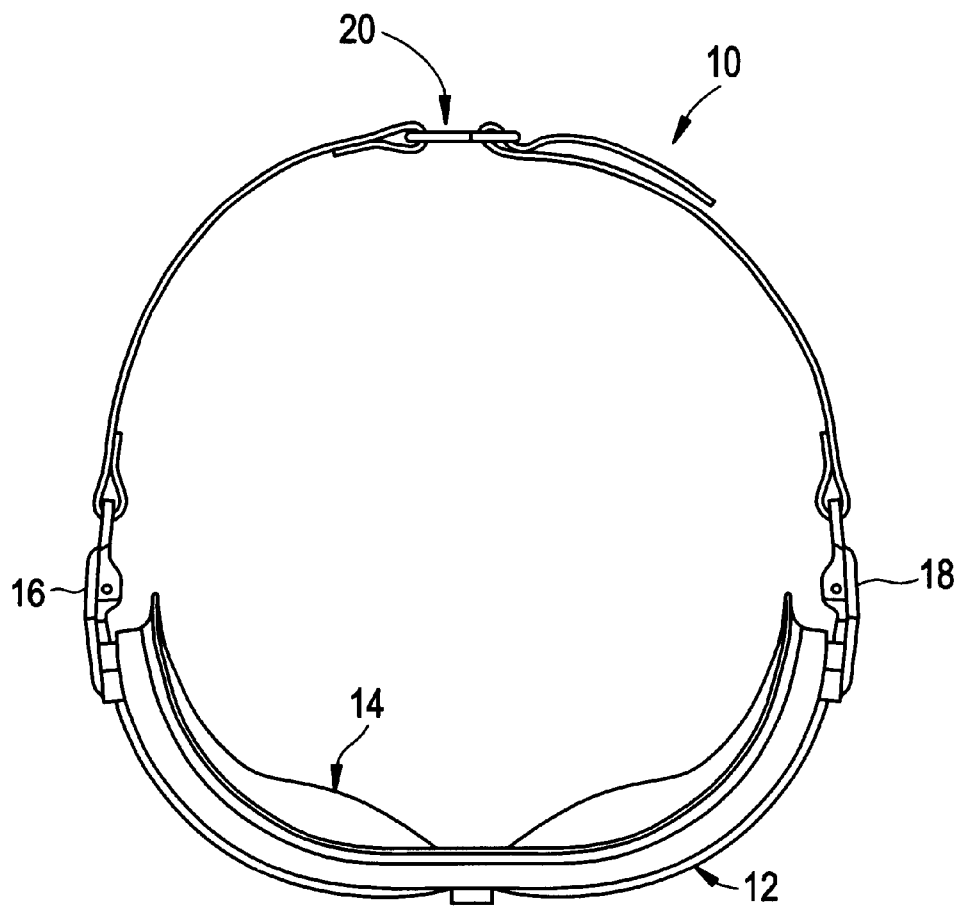
FIG. 1 is a top plan view of an exemplary protective eyewear with adjustable strap in accordance with the present invention.

Referring to FIG. 1, a protective eyewear with adjustable strap according to the present invention is shown generally at 10. The device 10 generally includes a lens 12, a frame 14, a pair of strap holding temples 16 and 18 and an adjustable strap assembly 20.

Figure 13:
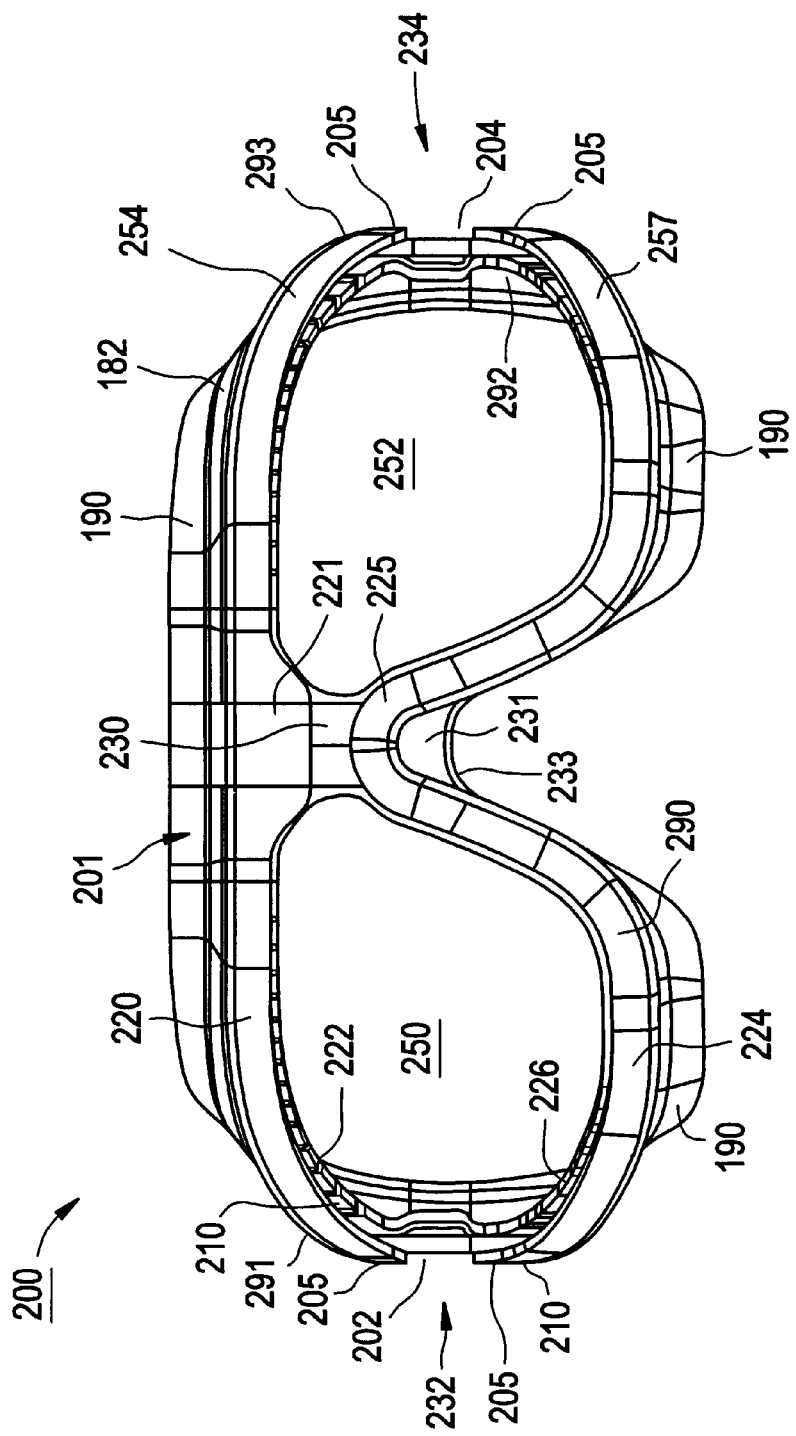
FIG. 13 is a front elevation view of another embodiment of the frame of FIG. 8.
Figure 14:
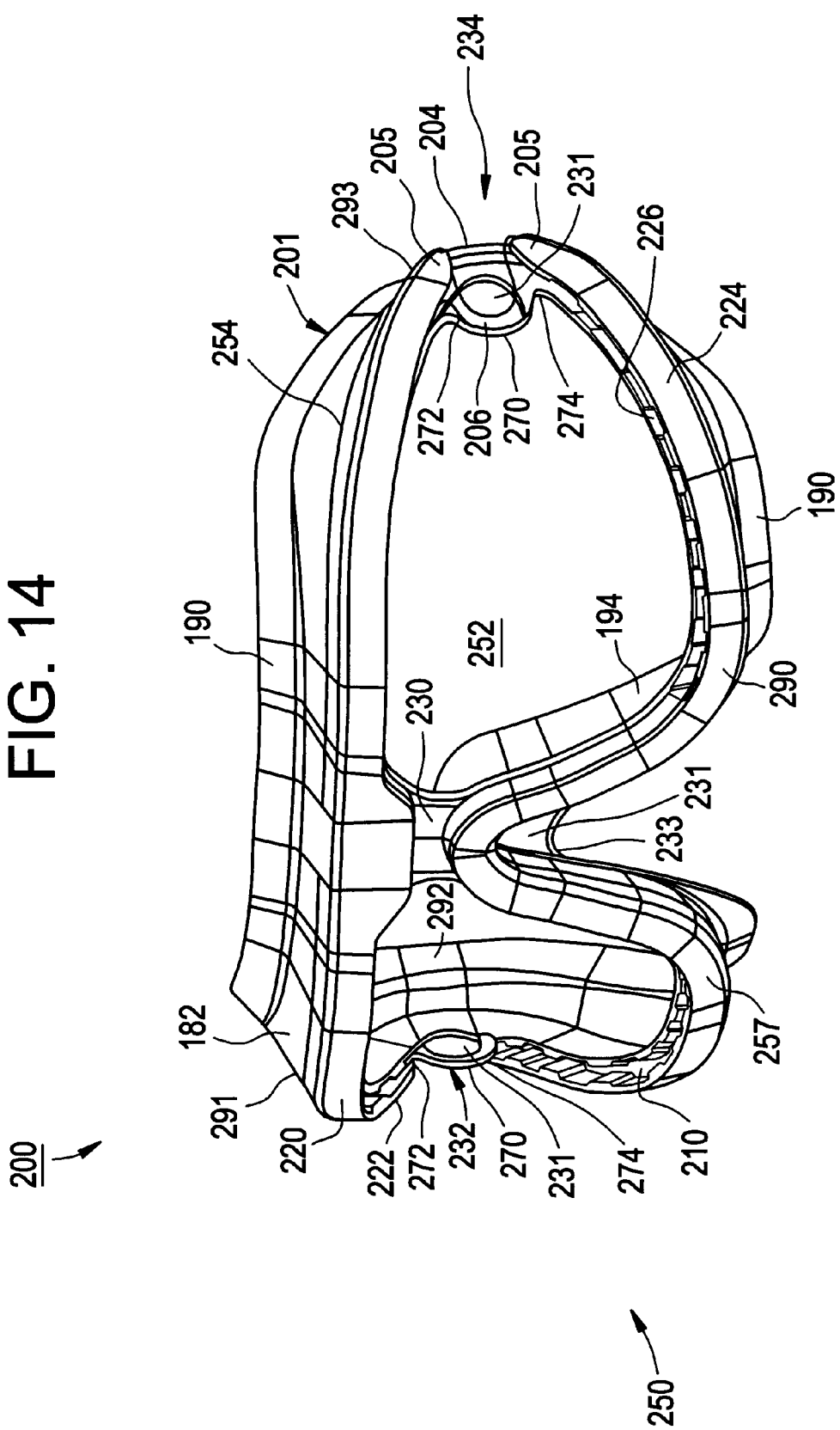
FIG. 14 is a front perspective view of the frame of FIG. 13.
Figure 15:
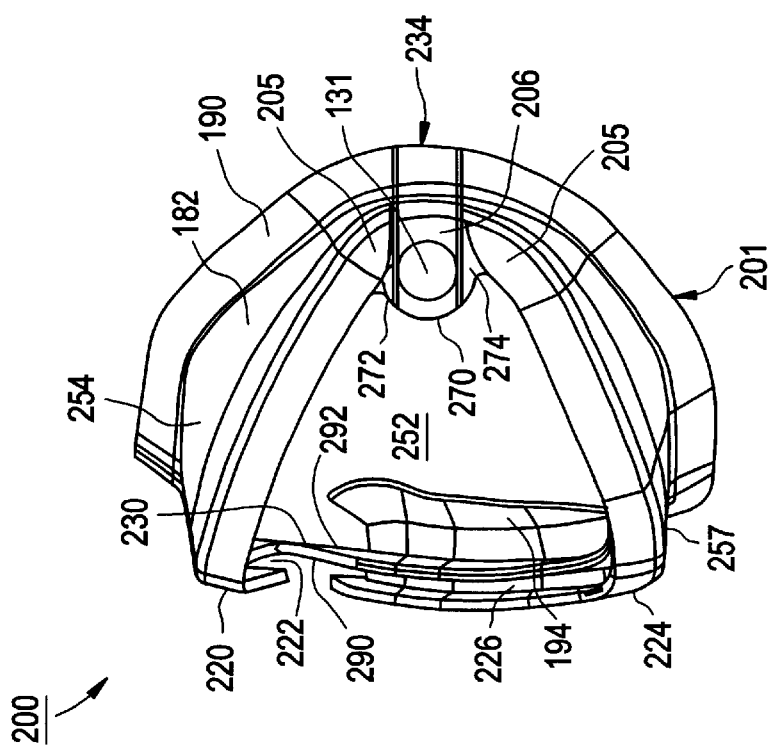
FIG. 15 is a side elevation view of the frame of FIG. 13.
Figure 16:
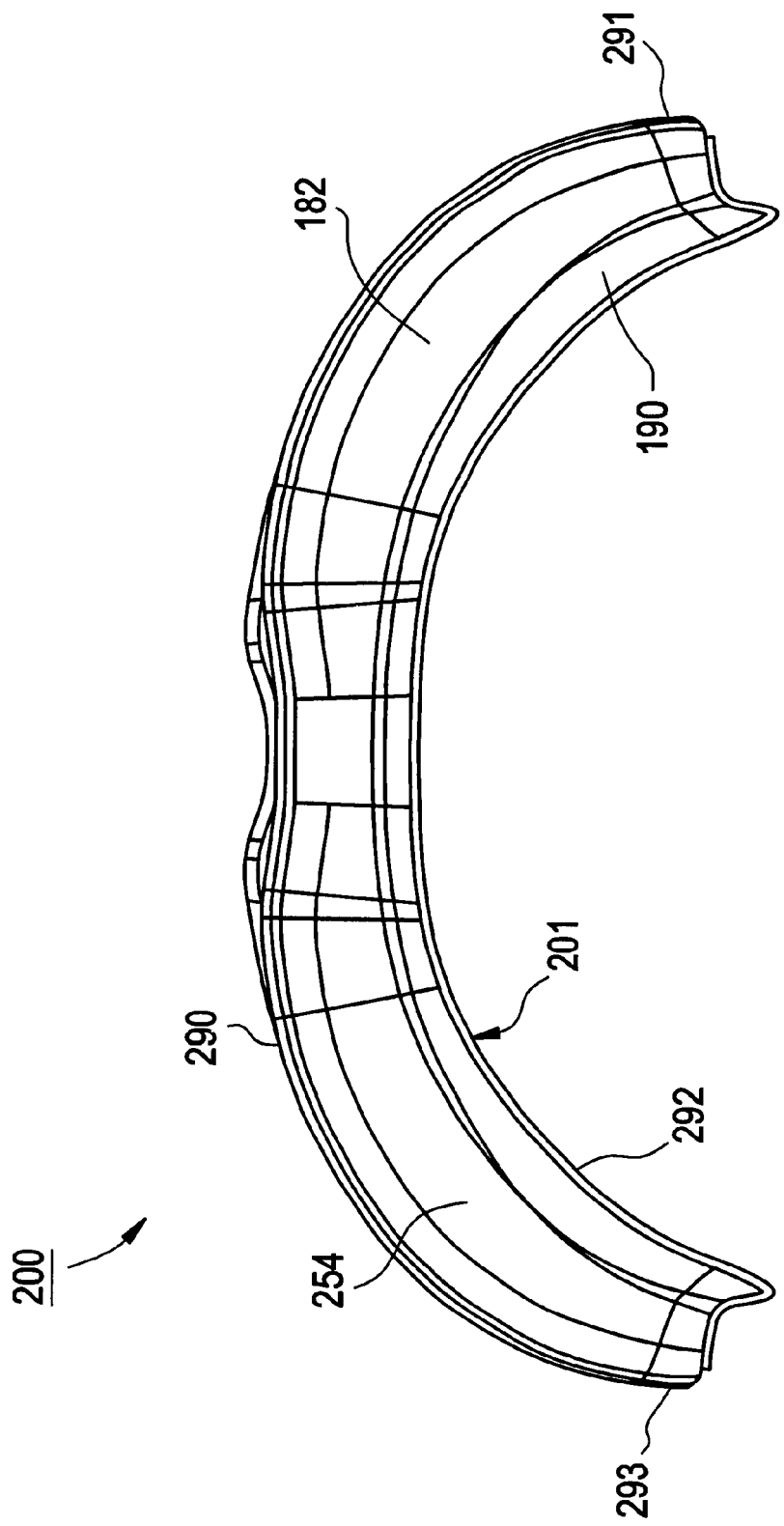
FIG. 16 is a top plan view of the frame of FIG. 13.
Figure 17:
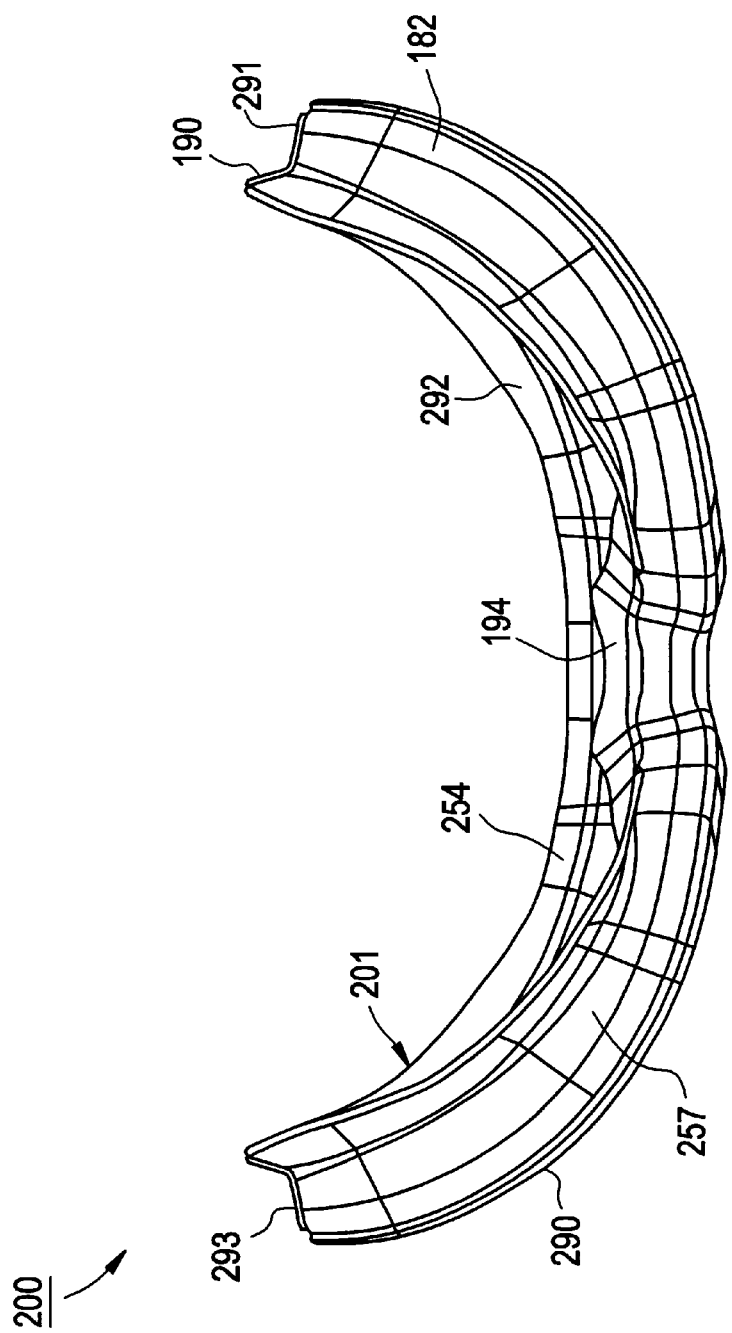
FIG. 17 is a bottom plan view of the frame of FIG. 13.

Lens 12 is preferably the unitary, plano lens depicted in FIGS. 13–15 of the aforementioned U.S. Ser. No. 08/641,901. However, it will be appreciated that lens 12 may consist of any other suitable protective lenses (having an alternative shape) including but not limited to the lenses depicted in FIGS. 1–6 and 11–12 of U.S. Ser. No. 08/641,901 or the lenses in the aforementioned U.S. Pat. Nos. 4,867,550; 4,741,611; 4,674,851; 4,859,048; 5,381,192 and 5,032,017.

As discussed in detail in aforementioned U.S. Ser. No. 08/641,901, lens 12 is preferably a plano lens wherein the plano lens comprises a front surface curvature which is created by rotating an aspheric shape about an axis which is offset from an axis of the aspheric shape. In a preferred embodiment, the aspheric shape is an ellipse or at least is an aspheric shape, a segment of which has an elliptical arc. This elliptical arc is rotated about an axis spaced (offset) some distance from a major or minor axis of the ellipse. In a more preferred embodiment, the ellipse is rotated about an axis spaced from and parallel to the major or minor axis of the ellipse, but in the same plane as the ellipse. The resulting surface of this preferred lens configuration will have a cross-section in the horizontal meridian which is a segment of an ellipse, and a cross-section in the vertical meridian which is a segment of a circle. A significant feature of the preferred lens configuration is that the surface generated is rotationally symmetric. Additionally, while plastic lenses are preferred, eyewear made of safety glass or any other suitable material can be utilized in conformance with this invention.

The eyewear of the present invention allows the user to hold the eyewear securely to the head by means of a unique adjustable strap or to use this adjustable strap to conveniently and securely attach the eyewear to another piece of safety equipment such as noise suppression ear muffs or communication head phones.

Figure 2:
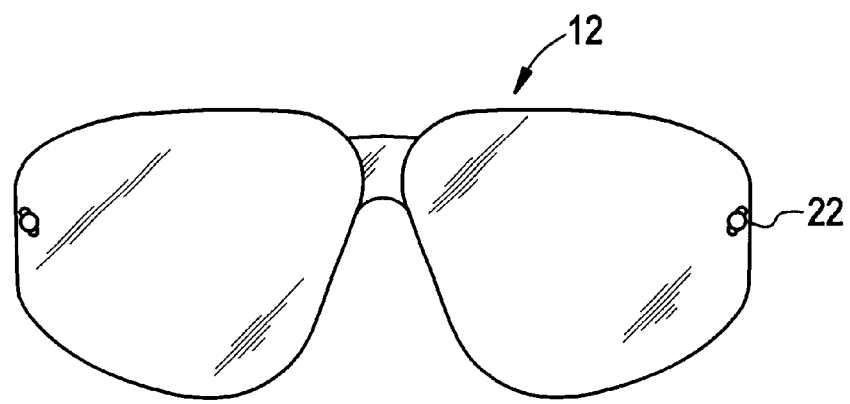
FIG. 2 is a front elevation view of a lens.
Figure 3:
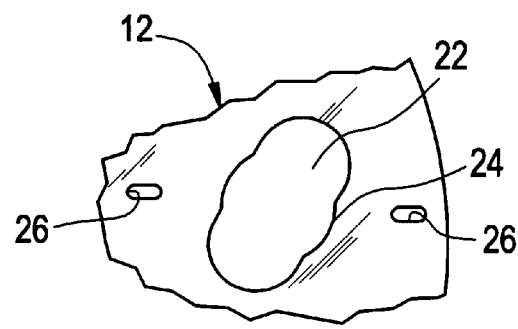
FIG. 3 is an enlarged view of a slot formed in the lens.

Referring to FIGS. 1–3 in which a preferred embodiment of the present invention, the lens 12 includes a slot 22 formed therein which cooperate with an end piece 30 (FIGS. 8–9) to provide adjustment of the pantoscopic angle of the eyewear. Slot 22 is generally oval shaped and has a center circular area 24. Projections 26 are formed on the surface of the lens 12 and extend away from the lens surface. Slot 22 permits lens 12 to be securely coupled to the frame 14 as will be described in greater detail hereinafter.

Figure 4:
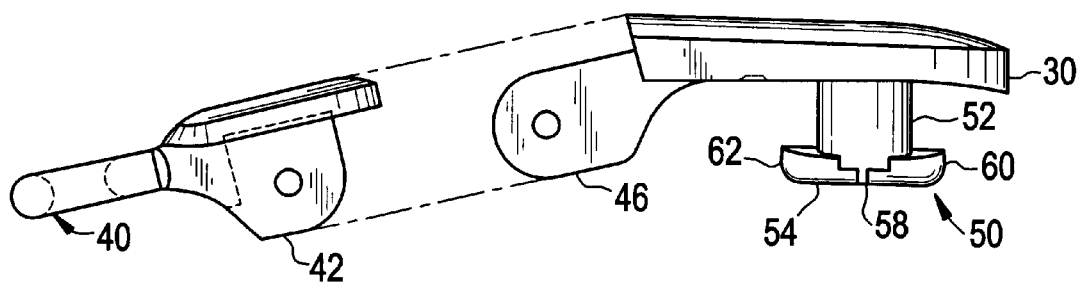
FIG. 4 is an exploded enlarged top plan view of a strap holding temple prior to assembly of the protective eyewear with adjustable strap in accordance with the present invention of FIG. 1.
Figure 5:
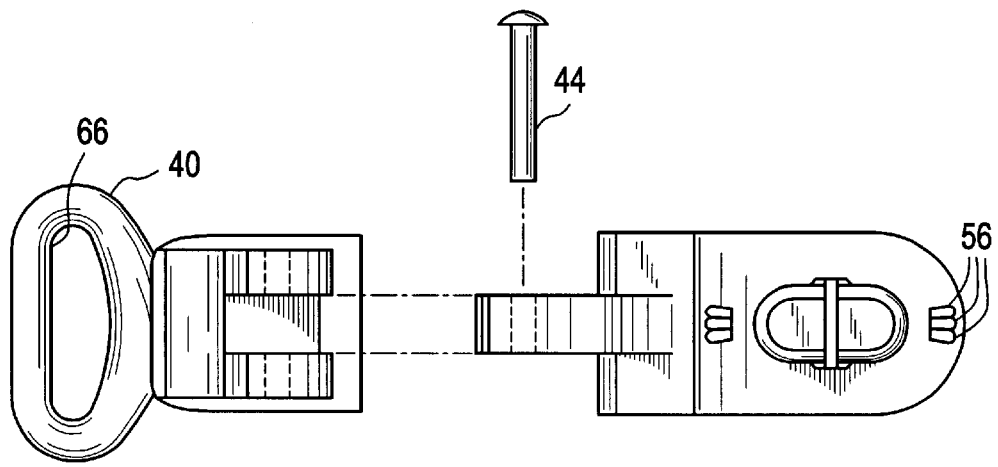
FIG. 5 is an exploded side-elevation view of the strap holding temple of FIG. 4.
Figure 6:
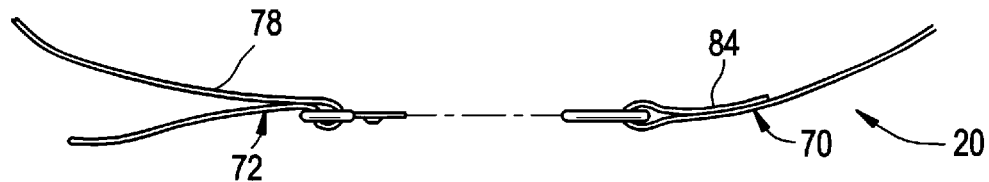
FIG. 6 is a partial exploded top plan view of a connective buckle and strap portion of the adjustable strap in accordance with FIG. 1.
Figure 7:
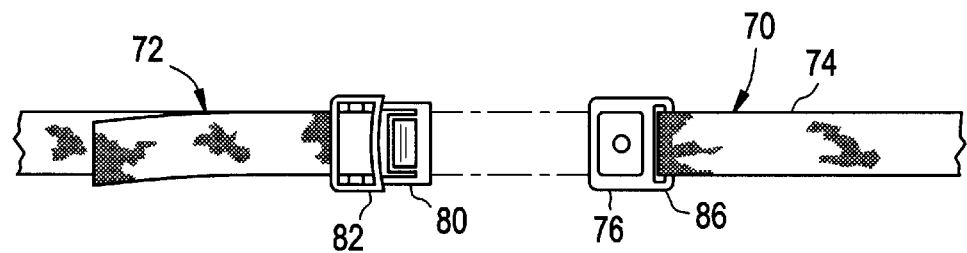
FIG. 7 is a partial side elevation view of the connective buckle and strap portion of FIG. 6.

FIGS. 1, and 4–5 show an adjustable strap holding element 40 which is used in the device 10 of the present invention. Strap holding element 40 includes a temple hinge 42. The temple hinge 42 is pivotally coupled to the end piece 30 with a pin 44 inserted through hinge element 46 to form a pivotable joint between end piece 30 and strap holding element 40. The pivotable joint between the end piece 30 and the strap holding element 40 allows the temples 14,16 to fold one upon the other to enable the eyewear to take up minimum space when eyewear 10 is stored or not in use. This pivotal joint also acts to enhance the fit of the eyewear to the user's head by appropriately conforming the strap and eyewear as required. The material used for end piece 30 and strap holding element 40 is preferably a suitable moldable plastic. In a preferred embodiment, strap holding temples 14, 16 are connected directly to the upper, outer edges of the lens 12.

The end piece 30 includes a post shown generally at 50 including a cylindrical neck 52 and a head 54. The end piece 30 includes recesses 56 that engage projections 26 (FIG. 3) formed on the exterior surface of the lens 12. A groove 58 is formed in the head 54 and a portion of the neck 52. In the illustrated embodiment, the groove 58 comprises a transverse groove extending across the head 54. The groove 58 may have any number of shapes including a v-shape (not shown) where the width of the groove at one end is greater than the width of the groove at the other end. It is therefore understood that alternative geometries may be used for groove 58. The groove 58 is formed generally perpendicular to the longitudinal axis of head 54 and extends across the entire head 54.

Referring now to FIGS. 1–12. The end piece 30 is coupled to the lens 12 by inserting the post 50 through the slot 22 and rotating the end piece 30. To adjust the pantoscopic angle of the eyewear, the wearer rotates the end piece 30 and aligns one pair of the recesses 56 with the projections 26 formed on the lens 12. The groove 58 allows the distal ends 60 and 62 along the longitudinal axis of the head 54 to flex away from the lens 12. This allows the end piece 30 to rotate within the lens 12 more easily. This is particularly useful when the end piece 30 is first rotated upon insertion of the end piece into the lens 12 and when the pantoscopic angle is adjusted. The end piece 30 is made from a resilient material and the distal ends 60 and 62 of the head 54 apply pressure to the lens 12 and hold the end piece 30 at the desired pantoscopic angle.

The pantoscopic angle features of the present invention are preferably identical to the pantascopic angle features of commonly assigned U.S. patent application Ser. No. 08/770, 920 filed Dec. 20, 1996 (all of the contents of which are incorporated herein by reference) except that the temple length adjustment housing 70 and temple tip 80 are replaced by the strap holding elements 40 and strap assembly 18 in the present invention. Therefore, reference is made to the application U.S. Ser. No. 08/770,920 for a additional details of the pantoscopic angle feature. The pantoscopic adjustment features assure for snug and comfortable fit especially when the protective eyewear of the present invention is combined with other safety devices.

The strap holding element 40 has a smooth loop 66 sized to accept adjustable strap assembly 20. Adjustable strap assembly 20 is comprised of a right hand buckle and strap assembly generally shown at 70 and a left hand buckle and strap assembly generally shown at 72. Right hand buckle and strap assembly 70 is comprised of a suitable length of strap 74 and a snap-in female portion of buckle 76. Likewise, left hand buckle assembly 72 is comprised of a suitable length of strap 78, the male portion of snap-in buckle 80 which mates with the female portion of buckle 76 and a known strap tightening fastener 82 for adjusting the left hand strap 78 to the desired position for a secure mounting of the eyewear on a person's head to assure a snug and comfortable fit.

Strap portion 74 and strap portion 78 are suitably sized as is known in the industry and is preferably of known stretchable materials. Half buckle 76 and half buckle 80 and strap tightening fastener 82 are commercially available and should be of such material and finish as required by the environment where used. Both half buckle 76 and half buckle 80 have known snap connectors that snap into detents that exist on the outside of the safety ear muffs, head phones or any other safety device used in conjunction with the present invention eyewear.

It should be noted that strap 78 is longer than strap 74 because the extra length of strapping is needed to provide adequate adjustment of the adjustable strap assembly 20. It should be further noted that the end 84 of right hand strap 74 is folded over a loop 86 of buckle (half) 76 and extends a suitable distance and is assembled to a portion of strap 74 by known methods such as adhesives, welding or other known means.

The frame 14 includes opposed sides 90 and 92 and includes opposing ends 91, 93. Lens 12 is retained on side 90 and side 92 forms a part of a skirt member generally indicated at 100. Frame 14 includes a plurality of ventilation channels 110 to allow ventilation into the device during use to prevent fogging of lens 12 and to provide comfort for the user. A lip 120 is provided along portions of the frame 14 to prevent dust and other unwanted particles and liquids from entering the device 10 during use. The side 90 receives the lens 12 and faces away from the user during use. The side 90 includes opposed protrusions 122, 124 disposed at a bridge portion 130 to locate and retain the lens 12 on the side 90. The frame 14 includes temple portions 132, 134, wherein each of the temple portions 132, 134 includes an upper and lower protrusion 136, 138, respectively which locate the lens 12 on the side 90 and retain the lens 12 by the contact of head portions 54 which face inward over the lens 12 when assembled. The frame 14 is preferably made of plastic and is resilient for ease of assembly. Preferably, protrusions 122, 124 also include head portions 140 which fit over the lens 12 to assist in a precise fit.

The frame 14 further includes openings 150, 152. The lip 120 is contoured and is disposed along part of an upper portion 154 and a lower portion 157 of the side 90. The lip 120 extends outward from the side 90 and tapers to its top 156. The lens 12 rests against the lip 120 at its outer periphery along a portion of its top and bottom. The plurality of vent channels 110 along an inner side 121 of the lip 120 and a surface 97 of the side 90. Preferably, the ventilation channels 110 comprise L-shaped recesses disposed along surface 97 of the side 90 and the inner side 121 of the lip 120. The L-shape of the ventilation channels 110 provides indirect ventilation to the face (and eyes) when the device 10 is worn. The ventilation channels 110 include recessed walls 160 which are separated by divider walls 162. Similarly, recessed walls 164 are separated by divider walls 166. Thus, air may enter from the side 90 of the frame 14 when lens 12 is assembled to the frame 14 by entering the ventilation channels 110 at recessed wall 164 and then traveling generally along recessed wall 160. Thus, ventilation occurs indirectly. In this manner, dust and other particles and liquid substances cannot fall between the lens 12 and the wearer's face because the lip 120 extends beyond the lens 12. Thus, ventilation is achieved while protection from dust and unwanted particles and liquids is optimized. It will be appreciated to those of ordinary skill in the art that the precise shape of the opening may be varied to allow for indirect ventilation.

Each temple portion 132, 134 includes an arcuate portion 170 connecting an upper temple portion 172 and a lower temple portion 174. Each temple portion 132, 134 actually defines a temple slot 131 formed in the frame 14 and partially defines by arcuate portion 170. Arcuate body portions 170 include inner arcuate surfaces 176. As described in greater detail hereinafter, inner arcuate surfaces 176 form a detachable attachment together with the head 54 of the end piece 30 on strap assembly 20. As head 54 is turned, it contacts the arcuate surface 176 to force respective ends 13, 15 of the lens 12 against protrusions 136, 138 to retain lens 12 onto side 112 by the contact of lens 12 against protrusions 136, 138 (and respective heads 54). This results in lens 12 being better retained in the frame 14.

The side 90 of the frame 14 further includes an outer perimetric rim 180 which extends around the outer periphery of the side 90 and extends outwardly away from the side 90 so as to provide a raised rim. Accordingly, the raised perimetric rim 180 extends about the lip 120, the protrusions 122, 124, 136, and 138 and openings 150, 152. The skirt 100 is formed by a beveled surface 182 which extends outwardly from the perimetric rim 180 to a flange element 190. The skirt 100 and the perimetric rim 180 serve to define the temple slot 131 which has an arcuate shape at the end defined by the arcuate portion 170.

The beveled surface 182 extends around the perimetric rim 180 and is preferably integrally formed with the remaining portions of the frame 14. The flange element 190 is provided at selected portions of the frame 14 and more specifically, the flange element 190 is provided at locations around the periphery of the frame 14. The flange element 190 forms a pair of opposing beveled edges 192 at a location generally below the bridge portion 130. At this location, the flange element 190 is inverted and extends inwardly away from the side 90. When the flange element 190 inverts, it forms a nose bridge portion 194 which is designed so that a nose of the user may rest therebetween comfortably.

Advantageously, the skirt 100 provides an effective seal against the face of the user when the device 10 is worn so that undesired foreign matter, including liquid substances, is prevented from entering into the eye area of the user underneath the eyewear being worn. More specifically, the skirt 100 provides an effective seal to help the wearer be protected from liquids and solid matter, e.g., particulate, which accidentally may be directed in a direction toward the eyes of the user. One particular application of device 10 is in a workplace where liquid splashes are possible and potentially damaging for the user of device 10 if the liquid is allowed to contact the eyes of the user. It will also be appreciated that the device 10 of the present invention likewise protects the eyes from solid particles and other foreign matter. Because the skirt 100 is preferably formed of the same material as the frame 14, the skirt 100 is formed of an elastomeric material which provides the desired seal characteristics. As is known in the art, the frame 14, including an integral skirt 100, may be formed by any number of fabrication processes including a molding process, e.g., injection molding. It being understood that while a one step molding process is the preferred technique to produce device 10, it is also equally within the scope of the present invention that the device 10 may be produced by forming the frame 14 without skirt 100 and then forming the skirt 100 by a subsequent molding process.

Referring now to FIGS. 1 and 13–17. In another embodiment of the present invention, a frame 200 may be used in conjunction with the lens 12, the pair of strap holding temples 16 and 18, and the adjustable strap assembly 20 to form a protective eyewear with adjustable strap according to the present invention.

The frame 200 includes opposed sides 290 and 292 and opposing ends 291 and 293. The side 290 receives the lens 12 and faces away from the user during use. The frame 200 includes a bridge portion 230 disposed substantially equidistant from the opposing ends 291 and 293. The bridge portion 230 also includes a nasal web 231 which is designed to rest on the nose of the wearer and provide additional wearing comfort to the user. The web 231 has a curved bottom edge 233 which seats against the nose. Preferably, the web 231 is integrally formed with the remaining portions of the frame 200. An opening 250 is disposed in the frame 200 between the bridge 230 and the end 291. An opening 252 is disposed between the bridge 230 and the end 293. The frame 200 further includes an upper portion 254 and a lower portion 257.

An upper lip 220 is disposed on the upper portion 254 of the frame 200 and extends from the end 291 to the end 293. The upper lip 220 is preferably a generally 'L' shaped protrusion that initially extends substantially perpendicularly from the side 290 of the frame 200 and then parallel to the side 290 towards the openings 250 and 252 so as to form an upper slot 222 for receiving the lens 12 as discussed herein.

A lower lip 224 opposes the upper lip 220 on the frame 200. The lower lip 224 is disposed on the lower portion 257 of the frame 200 and extends from the end 291 to the end 293. The lower lip 224 is likewise a generally 'L' shaped protrusion that initially extends substantially perpendicularly away from the side 290 of the frame 200 and then turns substantially parallel to the side 290 towards the openings 250 and 252 thus forming a lower slot 226 for receiving the lens 12 as discussed herein.

The upper and lower slots 222 and 226, respectively, are lined with a plurality of ventilation channels 210 to allow ventilation into the device during use to prevent fogging of the lens 12 and to provide comfort for the user. Preferably, the ventilation channels 210 comprise U-shaped recesses disposed within the upper and lower slots 222 and 226, respectively. The U-shaped channels 210 are disposed within the upper slot 222 upon the side 290 and the upper lip 220. The U-shaped channels are further disposed within the lower slot 226 upon the side 290 and the lower lip 224. The U-shaped channels 210 are disposed to abut the lens 12 when installed, as described herein, thus allowing air to enter the eyewear 10 from the side 290 providing ventilation to the face and eyes of the user. The individual ventilation channels 210 are constructed similarly to the ventilation channels 110 described herein with reference to FIG. 10 and include the recessed walls 160, 164 and the divider walls 162, 166. This construction allows air to ventilate the eyewear indirectly by traveling along the recessed walls 160, 164 in a U-shaped path around the edge of the lens 12 thereby preventing dust and particulate matter and liquids from directly falling into the eyewear.

The upper and lower lips 220 and 224, respectively, are preferably integrally formed as part of the frame 200 and, in an exemplary embodiment, are composed of a resilient thermoplastic material. Upon assembly of the eyewear utilizing the frame 200, the lens 12 is received on the side 290. The edge of the lens 12 is received within the upper and lower slots 222 and 226, respectively, with the lens 12 abutting the U-shaped ventilation channels 210. In other words, the lens 12 resiliently snaps into place within the upper and lower slots 222 and 226, respectively, because of the resilient nature of the frame 200 and the lens 12 is retainingly held therein by the upper and lower lips 220 and 224, respectively. Part of the upper lip 220 defines a first bridge tab 221 which serves to secure an upper bridge portion of the lens 12 and a portion 235 of the lower lip 224 acts as a second bridge tab for securing a lower bridge portion of the lens 12 when the lens 12 is received within the upper and lower slots 222, 226.

The frame 200 further includes a skirt 201 disposed on the side 292. The skirt 201 includes the nose bridge portion 194 described herein with reference to FIGS. 8 and 9. The nose bridge portion 194 is disposed on the skirt 201 beneath the bridge portion 230 of the frame 200.

Figure 8:
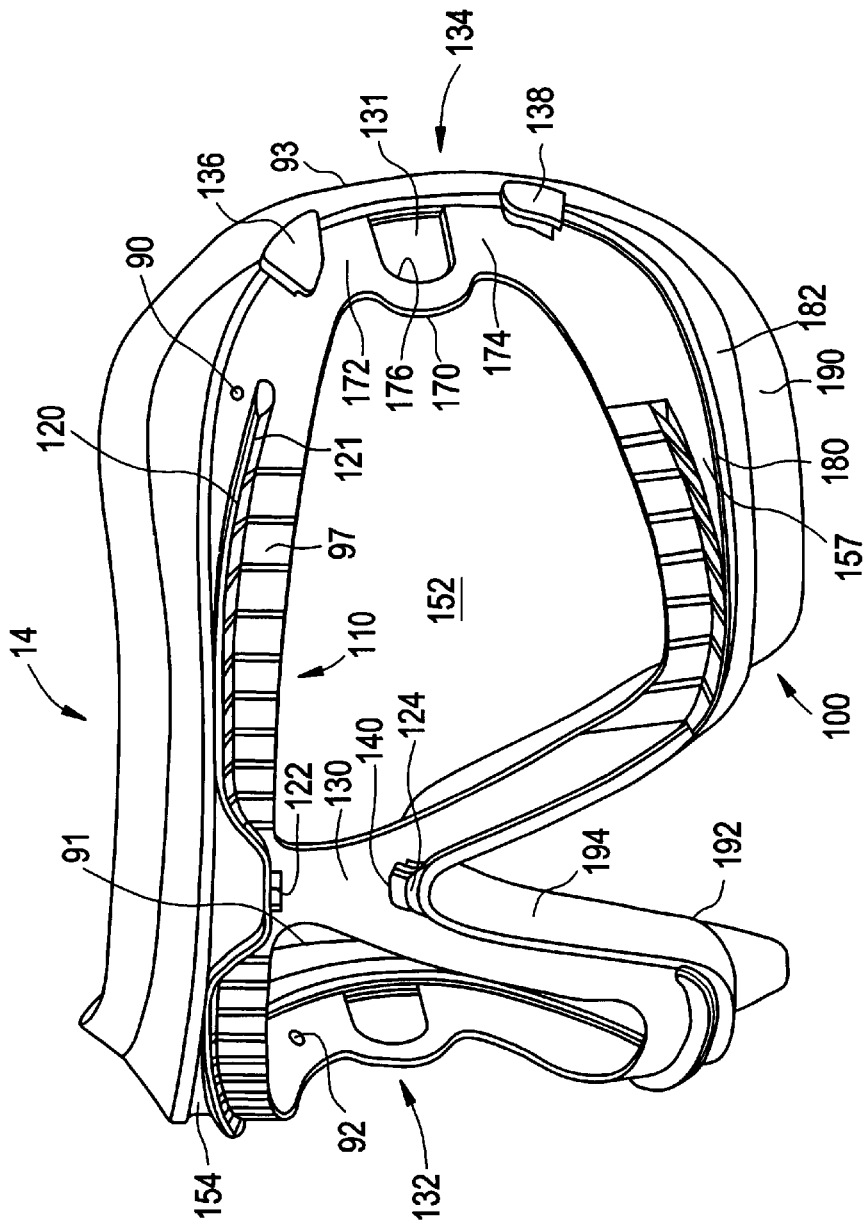
FIG. 8 is a front perspective view of a frame of the device of FIG. 1 prior to assembly.
Figure 9:
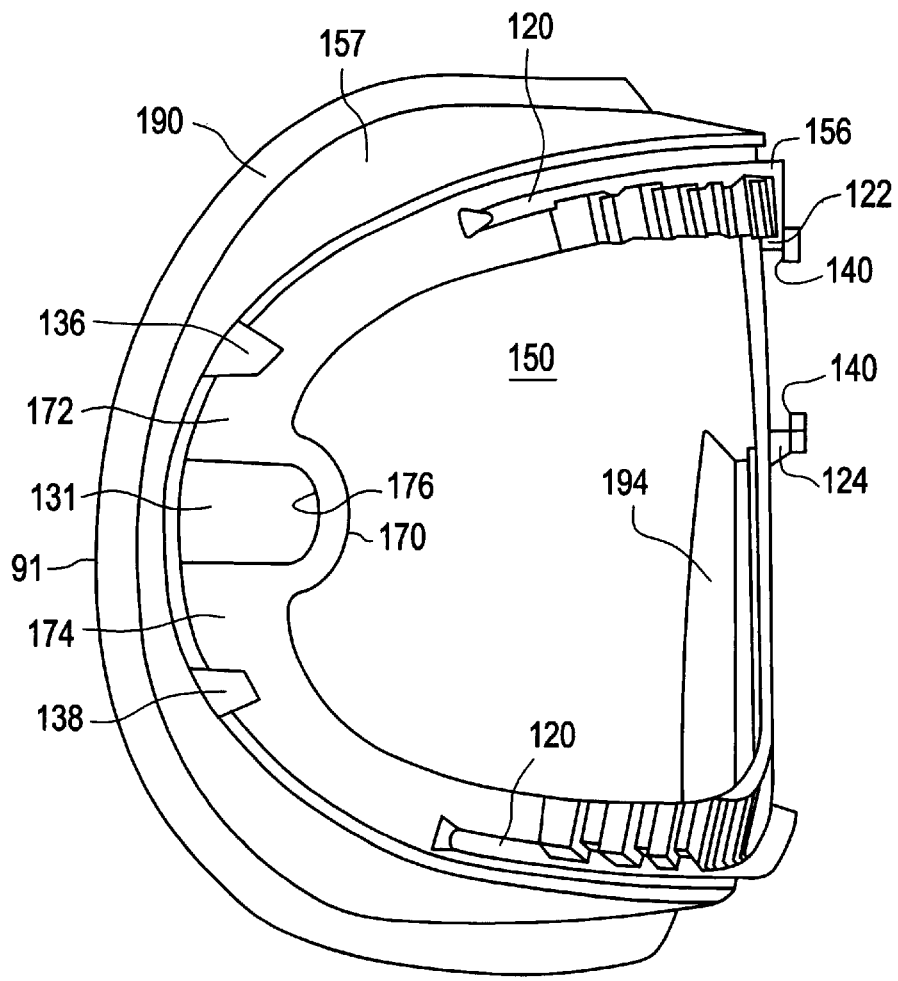
FIG. 9 is a left side view of the frame of FIG. 8.
Figure 10:
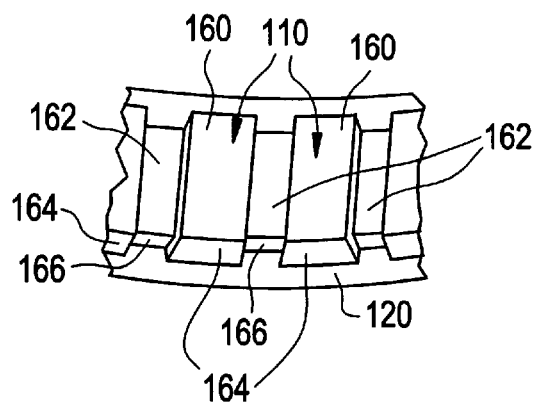
FIG. 10 is a perspective view of channels formed in the frame.
Figure 12:
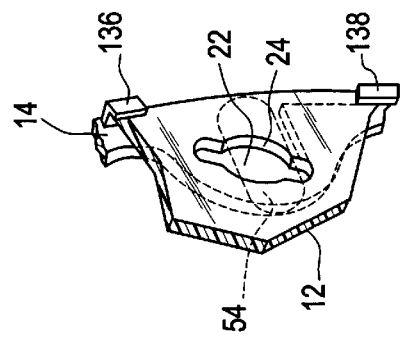
FIG. 12 is a perspective view of a slot in the lens of FIG. 2.
Figure 11:
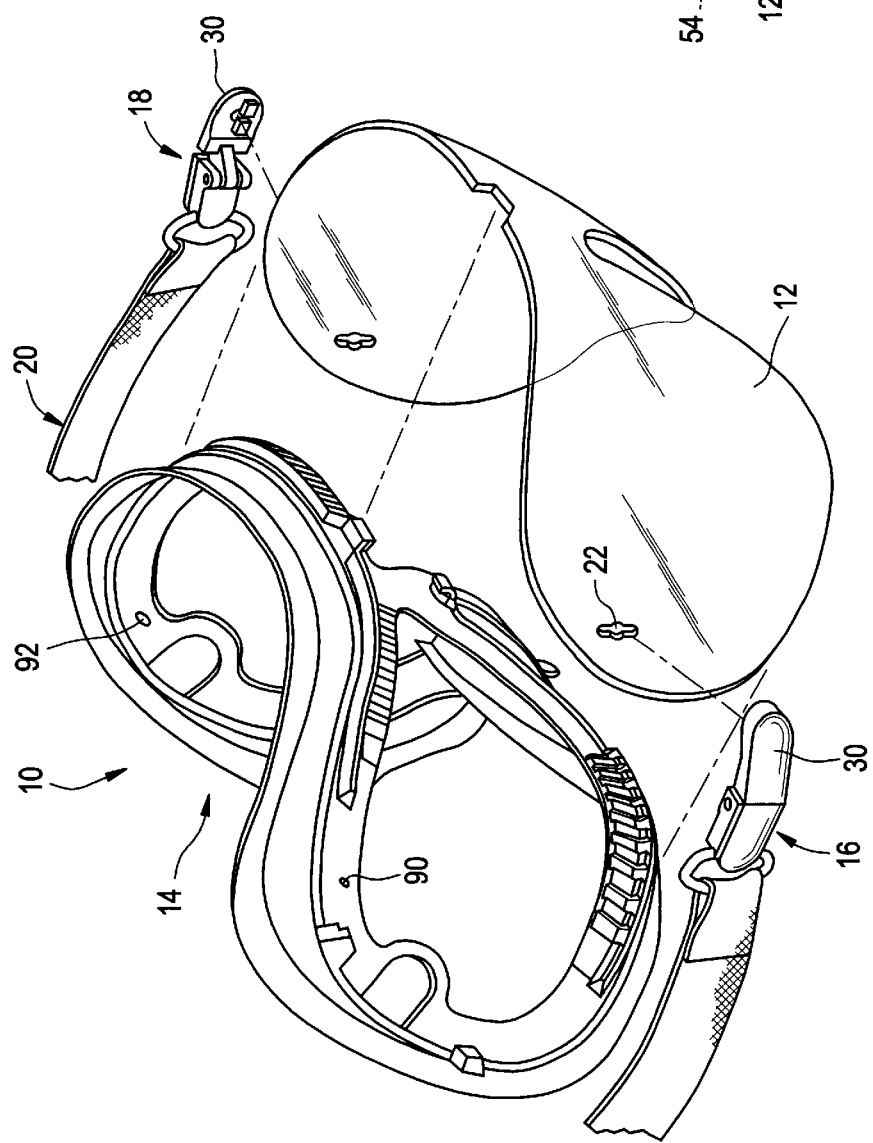
FIG. 11 is an exploded perspective view of the adjustable strap and the strap holding temple of FIGS. 4–6, and the lens of FIG. 2.

The skirt 201 also includes the beveled surface 182 described herein with reference to FIGS. 8 and 9. The beveled surface 182 is molded integrally about the frame 200. The beveled surface 182 is disposed between the upper and lower lips 220 and 224, respectively, and the flange element 190 taught herein with reference to FIGS. 8 and 9. The flange element 190 is provided at locations around the periphery of the frame 200 on the skirt 201 and comprises the nose bridge portion 194 beneath the bridge portion 230. The flange element 190 forms an effective seal against the face of the user when the present invention is worn so that undesired foreign matter, including liquids and solids, is prevented from entering into the eye area of the user. The flange element 190 may be composed of a resilient thermoplastic material to better form to the user's face.

The frame 200 further includes temple portions 232 and 234 disposed at the opposing ends 291 and 293, respectively. Each temple portion 232 and 234 includes an arcuate portion 270 connecting an upper temple portion 272 and a lower temple portion 274. The temple portions 232 and 234 and arcuate portions 270 define a temple slot 231 for receiving the head 54 of the post 50 of the end piece 30 when inserted in the lens 12 during assemblage of the eyewear utilizing the frame 200. The temple slots 231 may be a plurality of shapes sufficient for receiving the head 54 including, but not limited to, rectilinear and curvilinear shapes and combinations thereof As discussed above, the upper lip 220 and the lower lip 224 each terminate at the opposing ends 291 and 293, respectively. The upper lip 220 and the lower lip 224 are disposed at the opposing ends 291 and 293, respectively, so as to define end piece slots 202 and 204 which each receive the end pieces 30 during assembly and use of the eyewear utilizing the frame 200. The upper and lower lips 220 and 224, respectively, may contain tapperings 205 at the opposing ends 291 and 293 to facilitate reception of the end pieces 30. The temple portions 232 and 234 may include scores 206 on the side 290 of the frame 200 to further enhance reception of the end pieces 30.

The frame 200 may be composed of a resilient thermoplastic material to allow an elastic fit about the lens 12 and to provide comfort for the user while still maintaining sufficient eye protection from particulate matter and other common hazards associated with the use of the protective eyewear. The resilient thermoplastic material may comprise, for example, polyvinyl chloride (PVC), TPE, TPU, nylon, PCT, etc.

The present invention therefore offers eyewear which is designed to prevent liquids and solid matter, such as dust and other particulate, from contacting the eyes of the wearer. The eyewear may be worn in a multitude of settings and is easy to wear and manufacture.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. Eyewear comprising:
   a frame having a first side and an opposing second side and at least one ventilation channel formed in the first side, the frame having a skirt extending around a periphery of the frame for contacting a face of a user in a sealing manner, the skirt comprising a beveled surface extending outwardly from the first side of the frame and a flange member extending from the beveled surface for seating against the face, the frame having a pair of temple slots;
   a lens detachably coupled to the first side of the frame; and
   a pair of end pieces detachably attached to the lens by being inserted within openings formed in the lens and within the temple slots, the end pieces being inserted in a first position such that movement of the end pieces to a second position within the temple slots causes the end pieces to contact a portion of the frame for positioning and securing the lens relative to the frame.

2. The eyewear of claim 1, wherein the ventilation channel is a plurality of ventilation channels.

3. The eyewear of claim 1, wherein the ventilation channel is L-shaped.

4. The eyewear of claim 1, further comprising:
   a strap holding element hingedly attached to the end piece.

5. The eyewear of claim 1, wherein the temple slots are formed at opposing temple portions of the frame, the temple slots having an arcuate surface extending inwardly relative to sides of the frame.

6. The eyewear of claim 1, wherein the first side includes a first lip extending outwardly therefrom, the lip being adjacent to the outer periphery of the lens when the lens is attached to the frame.

7. The eyewear of claim 1, wherein the first side of the frame includes a first lip extending outward therefrom adjacent an upper periphery of the first side and a second lip extending outward therefrom adjacent a lower periphery of the first side, the first and second lips having a first surface substantially perpendicular to the first side of the frame, the first surface including a first ventilation channel formed therein, the first ventilation channel communicating with a second ventilation channel formed in the first side of the frame, the first and second ventilation channels being substantially perpendicular to one another.

8. The eyewear of claim 1, wherein the frame includes an upper temple protrusion and a lower temple protrusion disposed about each temple slot, the upper and lower temple protrusions for securing the lens to the first side of the frame.

9. The eyewear of claim 1, wherein the end piece includes a post including a head, the head being moved relative to the frame for further securing the lens to the first side of the frame.

10. The eyewear of claim 1, wherein the end piece in the second position, a head of the end piece contacts an arcuate surface partially defining the temple slot to position and secure the lens to the frame.

11. The eyewear of claim 1, wherein the skirt includes a nose bridge portion for contacting and seating against a nose of the user.

12. The eyewear of claim 1, wherein the flange member of the skirt has a first section which is outwardly directed away from the beveled surface around the periphery of the frame, the flange member having a second section in which the flange member is inwardly directed relative to the beveled surface.

13. The eyewear of claim 12, wherein the second section comprises a nose bridge section.

14. The eyewear of claim 1, wherein the flange element fluidly transitions from the first section to the second section.

15. The eyewear of claim 1, wherein the frame includes first and second projections formed at a bridge section of the frame for securing the lens to the frame.

16. The eyewear of claim 1, wherein the openings formed in the lens are positioned over the temple slots formed in the frame when the lens is received and secured to the first side of the frame.

17. The eyewear of claim 1, wherein the skirt is integrally formed with the frame.

18. Eyewear comprising:
    a frame having a first side and an opposing second side, the first side having an upper portion and a lower portion, the upper and lower portions each including at least one ventilation channel formed therein, the first side including an upper lip extending across the upper portion such that the upper lip and the first side define a first slot, an inner surface of the upper lip including at least one ventilation channel, the first side further including a lower lip extending across the lower portion such that the lower lip and the first side define a second slot, an inner surface of the lower lip including at least one ventilation channel, the frame having a skirt extending around a periphery of the frame for contacting a face of a user in a sealing manner, the frame having a pair of temple slots;
    a lens detachably coupled to the first side of the frame by inserting the lens into the first and second slots; and
    a pair of end pieces detachably attached to the lens by being inserted within openings formed in the lens and within the temple slots, the end pieces being inserted in a first position such that movement of the end pieces to a second position within the temple slots causes the end pieces to contact a portion of the frame for positioning and securing the lens relative to the frame.

19. The eyewear of claim 18, wherein the frame is formed of a resilient thermoplastic material to permit an elastic fit between the lens and the frame.

20. The eyewear of claim 18, wherein the skirt comprises a beveled surface extending outwardly from the first side of the frame and a flange member extending from the beveled surface.

21. The eyewear of claim 18, wherein the at least one ventilation channel is a plurality of U-shaped ventilation channels form in the first side and on the inner surface of each of the upper and lower lips.

22. The eyewear of claim 18, wherein each of the upper and lower lips comprises an L-shaped member extending from the first side such that each of the first and second slots is substantially U-shaped.

23. The eyewear of claim 18, wherein each of the upper and lower lips includes tapered ends disposed proximate the temple slots, the temple slots each including scorings for receiving the end pieces.

24. The eyewear of claim 18, wherein the frame further comprises a bridge portion disposed centrally between the pair of temple slots, the upper lip defining a first bridge tab for receiving and retaining an upper bridge portion of the lens, the lower lip defining a second bridge tab for receiving and retaining a lower bridge portion of the lens.

* * * * *

UNITED STATES PATENT AND TRADEMARK OFFICE
CERTIFICATE OF CORRECTION

| | | |
|---|---|---|
| PATENT NO. | : 6,276,795 B1 | Page 1 of 1 |
| APPLICATION NO. | : 09/542238 | |
| DATED | : August 21, 2001 | |
| INVENTOR(S) | : James Hall et al. | |

It is certified that error appears in the above-identified patent and that said Letters Patent is hereby corrected as shown below:

<u>Column 4</u>:
Line 52, after "for", delete "a".

Signed and Sealed this

Twenty-eighth Day of August, 2007

JON W. DUDAS
*Director of the United States Patent and Trademark Office*

UNITED STATES PATENT AND TRADEMARK OFFICE
CERTIFICATE OF CORRECTION

PATENT NO. : 6,276,795 B1 Page 1 of 1
APPLICATION NO. : 09/542238
DATED : August 21, 2001
INVENTOR(S) : James Hall et al.

It is certified that error appears in the above-identified patent and that said Letters Patent is hereby corrected as shown below:

Column 4:
Line 14, before "are", delete "14, 16" and insert therefor --16, 18--;
Line 50, after "strap assembly", delete "18" and insert therefor --20--;
Line 52, after "for", delete "a".

Signed and Sealed this

Eleventh Day of December, 2007

JON W. DUDAS
*Director of the United States Patent and Trademark Office*